United States Patent [19]

Tatsuno

[11] Patent Number: 4,779,003
[45] Date of Patent: Oct. 18, 1988

[54] APPARATUS FOR MEASURING A DROPLET SIZE DISTRIBUTION BASED ON THE SCATTERED LIGHT INTENSITY OF LIGHT APPLIED TO THE DROPLETS

[75] Inventor: Kyoichi Tatsuno, Yamato, Japan

[73] Assignee: Kabushiki Kaisha Toshiba, Kawasaki, Japan

[21] Appl. No.: 29,963

[22] Filed: Mar. 25, 1987

[30] Foreign Application Priority Data

Mar. 25, 1986 [JP] Japan .................................. 61-64703

[51] Int. Cl.$^4$ ...................... G01N 15/07; G01N 31/49
[52] U.S. Cl. ..................................... 250/575; 356/336
[58] Field of Search ................ 250/574, 575; 356/336, 356/338, 340, 341, 343

[56] References Cited

U.S. PATENT DOCUMENTS

| | | | |
|---|---|---|---|
| 3,704,951 | 12/1972 | Chupp | 250/574 |
| 4,023,909 | 5/1977 | Ross | 250/575 |
| 4,095,775 | 6/1978 | Hotham | 356/336 |
| 4,497,577 | 2/1985 | Sato et al. | 356/336 |
| 4,595,291 | 6/1986 | Tatsuno | 356/336 |

OTHER PUBLICATIONS

AIAA Paper No. 76-69. A Laser Diagnostic Technique For the Measurement of Droplet and Particle Size Distribution, Swithenbank et al. 1976.
The 1st International Conference on Liquid Atomization and Spray Systems (Tokyo, Japan). A Light Scattering Technique for Determining Droplet Size Distributions in Two-Phase Liquid-Dominated Nozzle Jets, Alger et al., 1978.

Primary Examiner—David C. Nelms
Assistant Examiner—William L. Oen
Attorney, Agent, or Firm—Oblon, Fisher, Spivak, McClelland & Maier

[57] ABSTRACT

A droplet size measuring apparatus of the forward scattering method, wherein particles to be measured in a scattering zone having a predetermined scattering path length are irradiated with parallel laser beams. The irradiated beams are scattered by the particles and the scattering beams are detected by the photodetectors arranged at predetermined scattering angles. The output of the photodetectors are input to an arithmetic operating unit, thus the intensity distribution $I(\theta)$ of the scattered beams is measured. The droplet size distribution $n(D)$ is calculated from the intensity distribution $I(\theta)$ using the following equation:

$$I(\theta) = \int \{I_0 \exp(-l \int c(D)n(D)dD \cdot \int i(D, \theta + \theta_l)n(D)d(D)\} dl$$

4 Claims, 4 Drawing Sheets

APPARATUS FOR MEASURING A DROPLET SIZE DISTRIBUTION BASED ON THE SCATTERED LIGHT INTENSITY OF LIGHT APPLIED TO THE DROPLETS

BACKGROUND OF THE INVENTION

This invention relates to an apparatus for measuring the droplet size distribution of very small particles.

This type of an apparatus is now being developed which measures the droplet size distribution of, for example, droplets of vapor in a turbine or droplets of fuel jetted into a combustion chamber, through the utilization of Mie scattering. Here the droplet size distribution means a relative distribution in the number of particles for a respective droplet size or diameter, i.e., a probability density function.

According to "Mie scattering" theory, the scattered light intensity $i(D,\theta)$ in a certain angular direction $\theta$ (at a scattering angle) when very monochromatic light beams, such as laser light, strike a spherical particle with a diameter D can be calculated. The scattered light intensity $I(\theta)$ of a group of spherical particles of various sizes can be expressed as a sum of respective scattered beams $i(D,\theta)$ on one particle of the diameter D, as set out below.

$$I(\theta) = \int i(D,\theta) n(D) dD \quad (1)$$

where n(D) denotes the droplet size distribution.

A method for measuring the droplet size distribution with the use of the principle of Equation (1) is called as the forward scattering method. This method is one type of the indirect measuring method which comprises:

(1) a first step of irradiating a group of particles with monochromatic parallel laser beams and measuring the angular distribution of the irradiation beams scattered on the group of particles—hereinafter referred to simply as the intensity distribution of the scattered beams; and (2) a second step of evaluating the droplet size distribution n(D) from the intensity distribution of the measured scattered beams $I(\theta)$ with the use of Equation (1).

Figure 5:
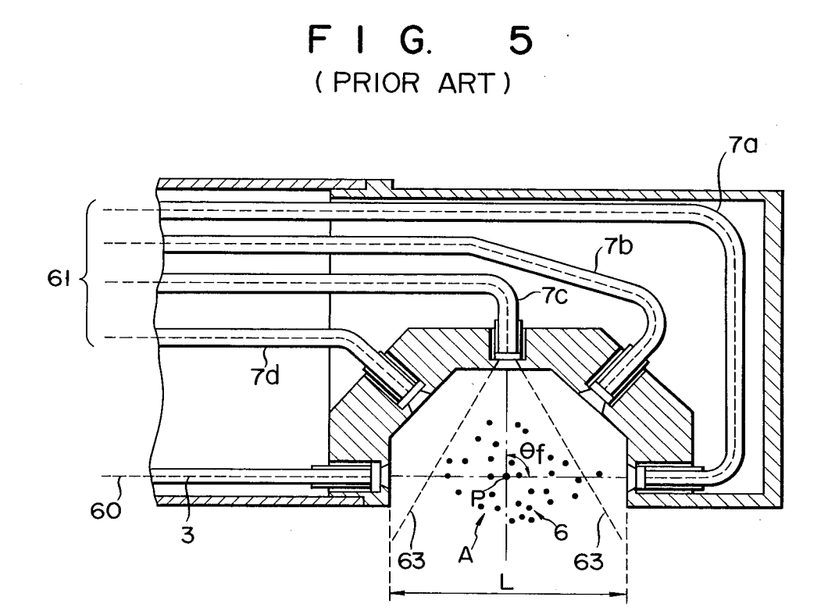
FIG. 5 is a view showing a conventional droplet size measuring apparatus.

FIG. 5 shows a conventional apparatus for measuring the droplet size by the aforementioned method. In this apparatus, output light 60 from a light source (not known), such as a laser is conducted via illumination optical fiber 3 into a scattering zone A and directed at the group of particles 6 in the scattering zone A. Beams 61 scattered at the respective scattering angles are conducted to photodetectors (not shown) via optical fibers 7a, 7b, 7c and 7d to measure the intensity distribution $I(\theta)$ of the scattered light. These optical fibers 7a, 7b, 7c, and 7d are arranged equidistant from the center P of the scattering zone A and for predetermined scattering angles.

In this apparatus, however, on account of the optical fibers 7a, 7b 7c, and 7d arranged at the predetermined scattering angles the optical fiber 7c, for example, receives not only the beams scattered at the scattering angle $\theta_f$ but also beams scattered on the particles occupied in a broader range as indicated by broken lines 63 in FIG. 5. As a result, the photodiode connected to the optical fiber 7c will receive the scattered beams at other than the scattering angle $\theta_f$ as well. Stated in a stricter way, $\theta$ in Equation (1) fails to indicate the set angles of optical fibers 7a, 7b, 7c, and 7d. However, no problem arises in the cases where the scattering path length L in the scattering zone A is shorter. The scattering path lenqth L may be made shorter in the case of measuring a larger droplet size since the intensity of the scattering light is adequate. For the smaller size of particles to be measured, on the other hand, the intensity of the scattering light is very small and, in order to increase the number of particles in the scattering zone A, it is necessary to increase the scattering path length L, failing to express the intensity distribution of the scattering light with Equation (1).

SUMMARY OF THE INVENTION

An object of this invention is to provide a droplet size measuring apparatus using the forward scattering method and which can accurately measure the droplet size distribution even for the smaller droplet size of particles to be measured and the longer scattering path length required for measuring smaller droplet sizes.

Another object of this invention is to provide a droplet size measuring apparatus which can measure the absolute droplet size distribution representing the distribution of absolute number of particles, as opposed to the relative droplet size distribution of particles.

According to this invention there is provided a droplet size measuring apparatus which comprises a light source for irradiating, with parallel light beams, a group of particles to be measured in a predetermined scattering path length, a measuring system having photodetectors arranged for respective scattering angles and measuring the intensity distribution of beams scattered on the group of particles, and a calculation unit for calculating the droplet size distribution of the particles in the group in accordance with a decrease of the parallel light beams within the scattering zone, scattering path length, and the measured intensity distribution of the scattered beams.

DETAILED DESCRIPTION OF THE PREFERRED EMBODIMENTS

Figure 1:
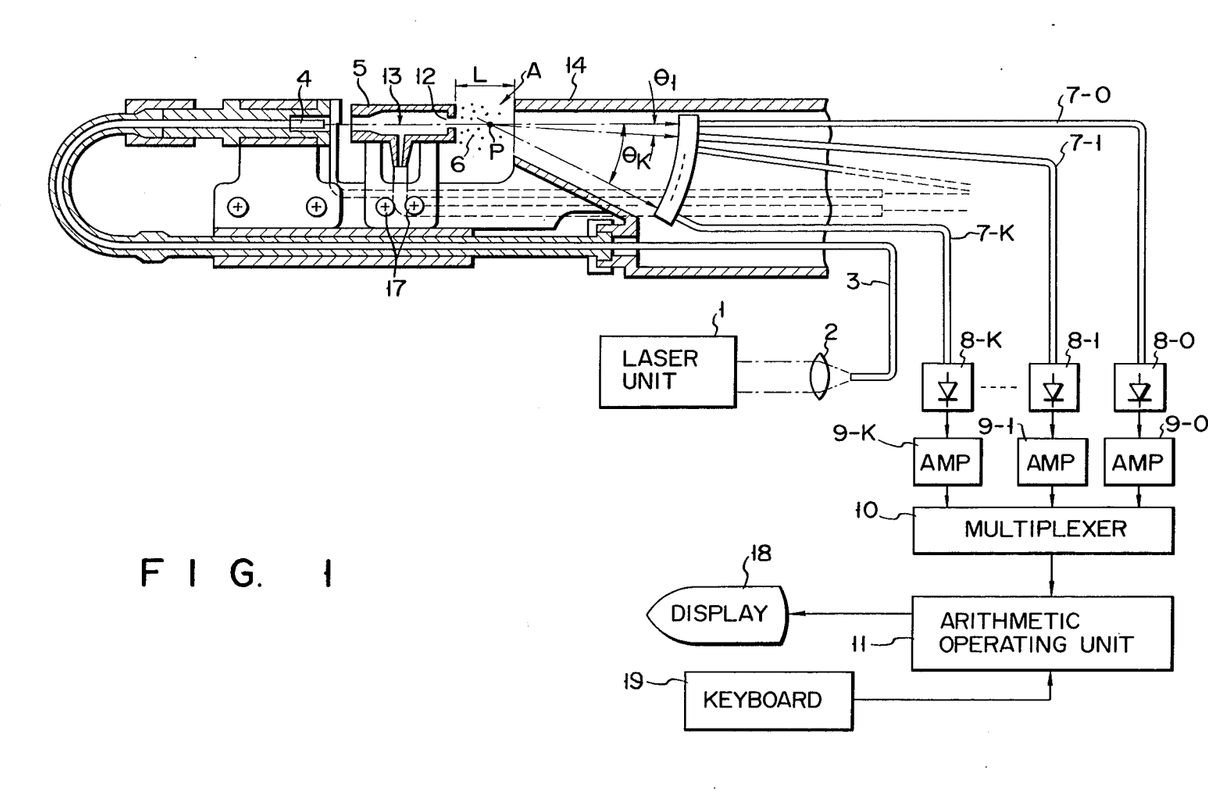
FIG. 1 is a view showing a droplet size measuring apparatus according to one embodiment of this invention.

FIG. 1 shows the whole arrangement of a droplet size measuring apparatus according to one embodiment of this invention. Output light from laser unit 1 (light source) is incident through lens 2 on optical fiber 3 for illumination. The laser light transmitted through optical fiber 3 emerges from the end of optical fiber 3 and is sent to collimator lens 4 where it illuminates, as parallel beam 13, a scattering zone A. Cylindrical spacer 5 is located between collimator lens 4 and the scattering zone A and adapted to be moved in the axial direction of parallel beam 13, when screws 17 are loosened, so that the scattering path length L is adjusted. Spacer 5 has hole 12 somewhat greater in diameter than the diameter of parallel beam 13. This is because parallel laser beam 13 is scattered and the scattering beams become a background noise in the measurement of the intensity distribution of the scattered beams by the particles 6 in group. To this end, the hole is formed in spacer 5 to prevent passage of the scattering light therethrough.

Figure 4A:
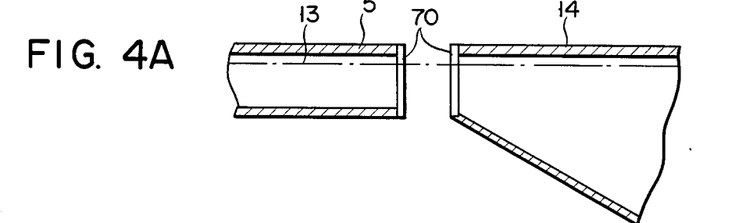
FIGS. 4A and 4B are views for restricting the scattering path length in the scattering zone by the embodiment of this invention.
Figure 4B:
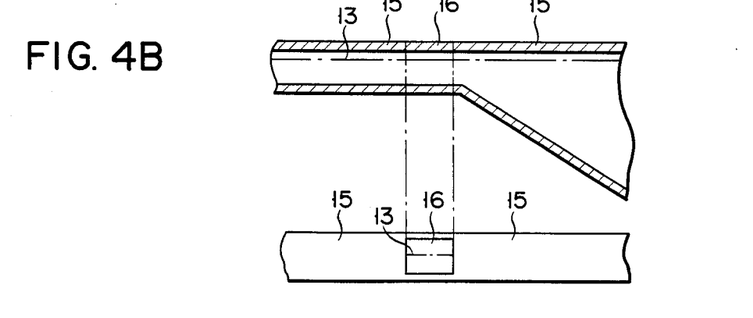

The scattering path length L in the scattering zone A where the group of particles 6 to be measured exists is restricted for the reason as will be set forth below. The restriction of the scattering path length L is made by, for example, confining the scattering path length L by glass plates 70 as shown in FIG. 4A or forming window 16 in part of pipe 15 to permit passage of parallel beam (illumination beam) 13 therethrough.

The beams which are scattered on the particles 6 present within the scattering zone A are received by receiving optical fibers 7-$i$ ($i=0 \sim K$, K: an arbitrary positive integer) located at predetermined scattering angles $0, \theta_1, \ldots, \theta_K$ where 0 denotes the transmission of light without being scattered. Then the received beams enter photodiodes 8-$i$. Optical fibers 7-$i$ are adapted to measure transmission light. Here it is to be noted that the scattering angles $\theta_1, \ldots, \theta_K$ represent angles viewed with the center P of the scattering zone A as a reference and that the light incident ends of respective optical fibers 7-$i$ are equidistant from the center P of the scattering zone A.

The light beams, after being converted by respective photodiodes 8-$i$ to electric currents, are supplied to respective amplifiers 9-$i$ where they are amplified as voltage signals. The voltage signals of the respective amplifiers 8-$i$ are supplied through a multiplexer 10 to arithmetic operating unit 11 and the result of the arithmetic operation is displayed on display 18. Keyboard 19 for inputting various data items is connected to arithmetic operation unit 11. Reference numeral 14 is a probe for including a measuring system of the intensity distribution of the scattered beam.

Figure 2:
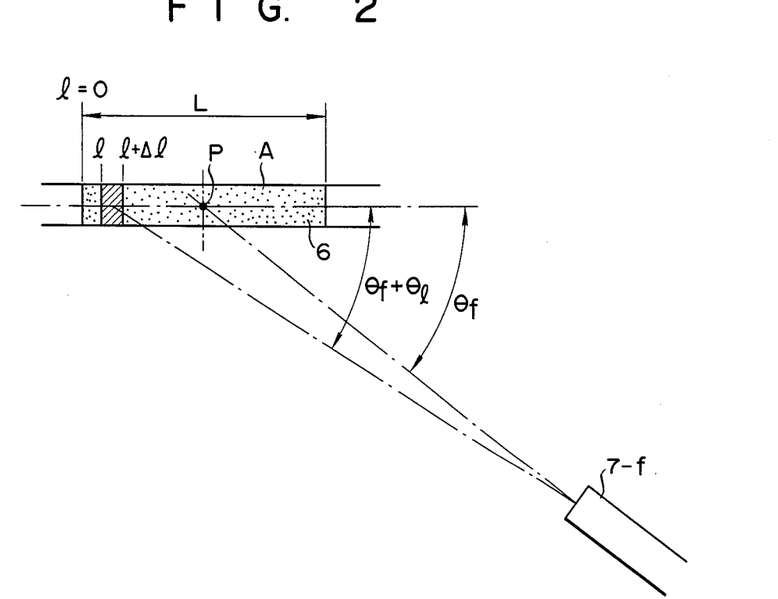
FIG. 2 is an explanatory view for explaining the principle on which the droplet size distribution is calculated.

An equation for providing the intensity of light received by optical fiber 7-$f$ will be obtained below with reference to FIG. 2, noting that optical fiber 7-$f$ is arranged at the scattering angle $\theta_f$. In a consideration of the decrease of the scattering beams caused by particles, the intensity $I_b(l)$ of the laser beams at the scattering position $l$ ($l = 0 \sim L$) is given by:

$$I_b(l) = I_0 \exp(-l \int c(D)n(D)dD) \quad (2)$$

where
$I_0$: the intensity of the beam at $l=0$
$c(D)$: the scattering cross section of a particle with a diameter D The term of $\exp(-l \int c(D)n(D)dD)$ represents the decrease of the scattering beams.

The intensity $\Delta I(l)$ of light scattered on particles which exist between the scattering positions $l$ and $l+\Delta l$ can be expressed as follows:

$$\Delta I(l) = I_b(l) \int i(D, \theta_f + \theta_l)n(D)dD \quad (3)$$

Substituting Equation (2) into Equation (3) yields:

$$\Delta I(l) = I_0 \exp(-l \int c(D)n(D)dD \cdot \int i(D, \theta_f + \theta_l)n(D)dD \quad (4)$$

With the scattering path length L restricted, the intensity $I(\theta_f)$ of the scattered light which is received by optical fiber 7-$f$ will be $$I(\theta_f) = \int_0^L \Delta I(l) dl \quad (5)$$

in which case optical fiber 7-$f$ is arranged at the scattering angle $\theta_f$.

When Equation (4) is substituted into Equation (5), then $$I(\theta_f) = \quad (6)$$

$$\int_0^L \{I_0 \exp(-l \int c(D)n(D)dD \cdot \int i(D, \theta_f + \theta_l)n(D)dD\}dl$$

showing the intensity of the scattered light which is received by optical fiber 7-$f$ arranged at the scattering angle $\theta_f$.

Arithmetic operation unit 10 solves Equation (6) for $n(D)$ with the measured value as $I(\theta_f)$ and evaluates the droplet size distribution. Here the solution of Equation (6) will be set out in more detail. Equation (6) is solved by the following two methods:
(1) assuming the distribution function of $n(D)$ or
(2) dividing the integration interval of the integrating equation in Equation (6) and letting Equation (6) approximate through the use of the simultaneous equations.

The method (1) will be explained below, assuming the distribution function of $n(D)$.

With one of the logarithmic-normal distribution, normal distribution, Rossin-Rammler, and the like properly selected as the distribution function of $n(D)$, then $$n(D) = N_0 n_r(D) \quad (7)$$

where
$N_0$: the particle density
$n_r(D)$: the distribution function selected.

With the logarithmic-normal distribution selected, $$n_r(D) = \frac{1}{\sqrt{2\pi D l_n B}} \exp\left[-\frac{(l_n D - l_n A)^2}{2 l_n^2 B}\right] \quad (8)$$

where
D: the droplet size
$\pi$: the ratio of the circumference of a circle to its diameter
A,B: the distribution parameters $I(\theta)$ is evaluated with respect to a plurality of $\theta_s$. Substituting Equation (8) into Equation (7), and Equation (7) into Equation (6), results in determining the $N_0$, A and B through the use of the least squares method. In this case, $n(D)$ is evaluated from Equation (7).

The method (2) will now be explained below.
With the integration interval of the particle size D as $[D_{min}, D_{max}]$, Equation (6) becomes $$I(\theta_f) = \int_0^L \left\{ I_0 \exp\left(-l \int_{D_{min}}^{D_{max}} c(D)n(D)dD\right) \times \int_{D_{min}}^{D_{max}} i(D, \theta_f + \theta_l)n(D)dD \right\} dl \quad (9)$$

Rearranging the order of the integration with respect to l and D, $$I(\theta_f) = \int_{D_{min}}^{D_{max}} \left[ \int_0^L \left\{ I_0 \exp\left(-l \int_{D_{min}}^{D_{max}} c(D)n(D)dD \right) \times i(D, \theta_f + \theta_l) \right\} dl \right] n(D)dD \quad (10)$$

With $[D_{min}, D_{max}]$ N-divided, Equation(10) becomes $$I(\theta_f) = \sum_{j=1}^{N} \int_{D_{j-1}}^{D_j} \left[ \int_0^L \left\{ I_0 \exp\left(-l \int_{D_{min}}^{D_{max}} c(D)n(D)dD \right) \times i(D, \theta_f + \theta_l) \right\} dl \right] n(D)dD \quad (11)$$

Here, $D_0 = D_{min}$ and $D_N = D_{max}$.

If it is assumed that $n(D)$ is constant within the subinterval $[D_{j-1}, D_j]$ and $$\int_{D_{j-1}}^{D_j} n(D)dD$$

is replaced by $n(D_j)$, then the right term of Equation (11) becomes $$\int_{D_{j-1}}^{D_j} \left[ \int_0^L \left\{ I_0 \exp\left(-l \int_{D_{min}}^{D_{max}} c(D)n(D)dD \right) i(D, \theta_f + \theta_l) \right\} dl \right] n(D)dD = \left[ \int_{D_{j-1}}^{D_j} \left\{ \int_0^L I_0 \exp\left(-l \int_{D_{min}}^{D_{max}} c(D)n(D)dD \right) i(D, \theta_f + \theta_l)dl \right\} dD \right] n(D_j) \quad (12)$$

If part of the right term of Equation (12) is put in the form of $$i_s(D_j, \theta_f, n(D)) \triangleq \int_{D_{j-1}}^{D_j} \left\{ \int_0^L I_0 \exp\left(-l \int_{D_{min}}^{D_{max}} c(D)n(D)dD \right) i(D, \theta_f + \theta_l)dl \right\} dD \quad (13)$$

then Equation (11) will be $$I(\theta_f) = \sum_{j=1}^{N} i_s(D_j, \theta_f, n(D))n(D_j) \quad (14)$$

With the measuring point $\theta_f$ of the intensity of the scattering light as $\theta_1, \theta_2, \ldots, \theta_K$, $$\begin{pmatrix} I(\theta_1) \\ I(\theta_2) \\ \vdots \\ I(\theta_K) \end{pmatrix} = \begin{pmatrix} i_s(D_1,\theta_1,n(D)), & i_s(D_2,\theta_1,n(D)), & \ldots & i_s(D_N,\theta_1,n(D)) \\ i_s(D_1,\theta_2,n(D)), & i_s(D_2,\theta_2,n(D)), & \ldots & i_s(D_N,\theta_2,n(D)) \\ \vdots & \vdots & & \vdots \\ i_s(D_1,\theta_K,n(D)), & i_s(D_2,\theta_K,n(D)), & \ldots & i_s(D_N,\theta_K,n(D)) \end{pmatrix} \times \begin{pmatrix} n(D_1) \\ n(D_2) \\ \vdots \\ n(D_N) \end{pmatrix} \quad (15)$$

Here $$I \triangleq \begin{pmatrix} I(\theta_1) \\ I(\theta_2) \\ \vdots \\ I(\theta_K) \end{pmatrix} \triangleq \begin{pmatrix} I_1 \\ I_2 \\ \vdots \\ I_K \end{pmatrix} \quad (16)$$

$$G(n) = \begin{pmatrix} i_s(D_1,\theta_1,n(D)), & i_s(D_2,\theta_1,n(D)), & \ldots & i_s(D_N,\theta_1,n(D)) \\ i_s(D_1,\theta_2,n(D)), & i_s(D_2,\theta_2,n(D)), & \ldots & i_s(D_N,\theta_2,n(D)) \\ \vdots & \vdots & & \vdots \\ i_s(D_1,\theta_K,n(D)), & i_s(D_2,\theta_K,n(D)), & \ldots & i_s(D_N,\theta_K,n(D)) \end{pmatrix} \quad (17)$$

$$n \triangleq \begin{pmatrix} n(D_1) \\ n(D_2) \\ \vdots \\ n(D_N) \end{pmatrix} \triangleq \begin{pmatrix} n_1 \\ n_2 \\ \vdots \\ n_N \end{pmatrix} \quad (18)$$

Here Equation (17) is represented as G(n) since it is the function of n. Equation (15) can be expressed by the following simultaneous equations with n as an unknown number as in the case of Equations (16) to (18)

$$I = G(n) \cdot n \quad (19)$$

noting that Equation (19) can be solved based on the Newton's method. With $G(n)^*$ put as the transverse matrix of $G(n)$, the least squares solution satisfies $$G(n)^* I - G(n)^* G(n) \cdot n = 0 \quad (20)$$

If $G(n)$ is regarded as being a constant in the neighborhood of $n_0$ (an initial value of n), then the approximation of Equation (20) can be made by the linear equation.

$$G(n_0)^* I - G(n_0)^* G(n_0) \cdot n = 0 \quad (21)$$

Equation (21) is solved as:

$$n = (G(n_0)^* G(n_0))^{-1} G(n_0)^* I \quad (22)$$

The nonlinear equation of Equation (20) can be solved for n if the solution n of Equation (22) is put as $n_0$ and the calculation of Equation (22) is repeated until the absolute value of a difference between n and $n_0$ satisfies the following relation:

$$|n_0 - n| < \epsilon \quad (23)$$

It is, therefore, possible to evaluate the distribution $n(D_j)$ of the droplet sizes per the subinterval $[D_{j-1}, D_j]$ of the particle sizes. In Equation (23), $\epsilon$ denotes a very small number for convergence judgment.

The approximation of $G(n)$, which may be regarded as being constant for n in the neighborhood of $n_0$ will be given below.

Now an arbitrary element $i_s(D_g, \theta_p, n(D))$ of $G(n)$ will be considered, noting that $i_s$ is given by Equation (13).

Rearranging the order of the integration of Equation (13), $$i_s(D_j, \theta_f, n(D)) = \int_0^L \left( I_0 \exp\left( -l \int_{D_{min}}^{D_{max}} c(D) n(D) dD \right) \int_{D_{j-1}}^{D_j} i(D, \theta_f + \theta_l) dD \right) dl \quad (24)$$

Here $$\int_{D_{min}}^{D_{max}} c(D) n(D) dD = \sum_{p=1}^{N} c_p n_p \Delta D \quad (25)$$

Substituting this approximation (Equation (25)) into Equation (24) gives:

$$i_s(D_j, \theta_f, n(D)) = \quad (26)$$

$$\int_0^L I_0 \exp\left( -l \sum_{p=1}^{N} c_p n_p \Delta D \right) \int_{D_{j-1}}^{D_j} i(D, \theta_f + \theta_l) dD \; dl$$

Differentiating Equation (26) with $n_g = n(D_g)$ it follows that $$\frac{\partial i_s(D_j, \theta_f, n(D))}{\partial n_g} = \quad (27)$$

$$\int_0^L \left( I_0 \exp\left( -l \sum_{p=1}^{N} c_p n_p \Delta D \right)(-l c_g \Delta D) \times \right.$$

$$\left. \int_{D_{j-1}}^{D_j} i(D, \theta_f + \theta_l) dD \right) dl$$

where $c_g = c(D_g)$.

In Equation (27), the near maximal values are taken as L, $c_g$ and $\Delta D$ given below:

$L = 10^{-2}$ (m)

$c_g = 6.3 \times 10^{-8}$ m² (the scattering cross section of polystyrene particles in water which are illuminated with He-Ne laser beam of 200 $\mu m \phi$)

$\Delta D = 20 \times 10^{-6}$ m

In this case, $$L c_g \Delta D = 1.3 \times 10^{-14} \quad (28)$$

Therefore $$\left| \frac{\partial i_s(D_j, \theta_f, n(D))}{\partial n_g} \right| \leq 1.3 \times 10^{-14} \, i_s(D_j, \theta_f, n(D)) \quad (29)$$

It may be assumed that $i_s(D_j, \theta_f, n(D))$ is constant in the neighborhood of $n_0$. Obtaining the initial value $n_0$ on the bases of Equation (22) where $$\exp\left( -l \int_{D_{min}}^{D_{max}} c(D) n(D) dD \right) = 1 \quad (30)$$

yields a comparatively better approximation value.

Figure 3:
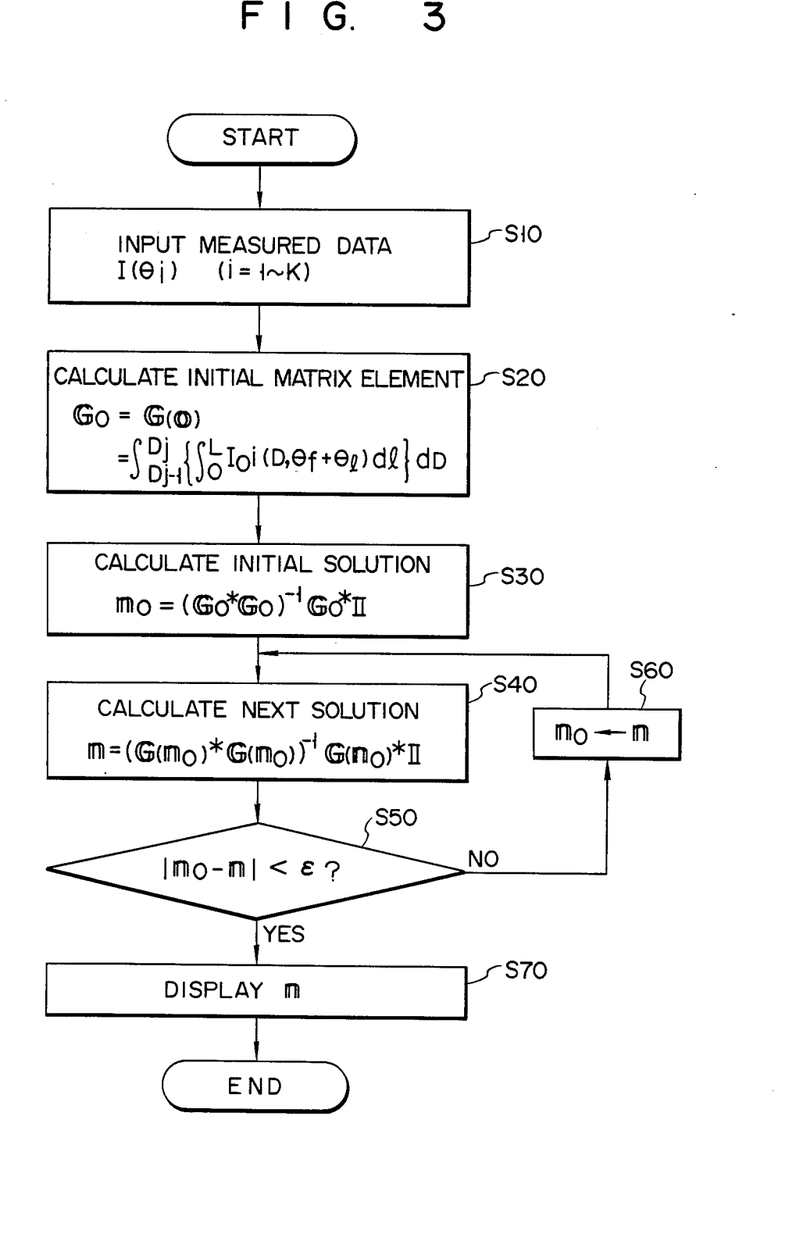
FIG. 3 is a flowchart showing the steps of calculating the droplet size distribution on the apparatus according to this invention.

The algorithm of this method (2) for obtaining the approximation of Equation (6) with the use of the simultaneous equations will be explained below with reference to the flowchart of FIG. 3.

At step S10 the intensity distribution $I(\theta_i)$ of the scattered beam obtained at photodiode $8\text{-}i$ is input to arithmetic operating unit 11, noting that $$\theta_i = \theta_1 \sim \theta K$$

At step S20, the matrix element of the initial value $G_0 = G(0)$ is calculated with the use of Equation (13). At step S30 the initial value $n_0$ of n is calculated through the substitution of $G_0$ into Equation (22). At step S40, n is calculated from Equation (22) with the use of $n_0$. At step S50, it is determined whether or not the absolute value $|n_0 - n|$ of a difference between n and $n_0$ is smaller than $\epsilon$. If the absolute value of $|n_0 - n|$ is not smaller than $\epsilon$, then the process goes to step S60 where $n_0 \leftarrow n$ and step S60 goes back to step S40 where n is again evaluated from Equation (22). If at step S50 it is determined whether the absolute value of $|n_0 - n|$ is smaller than e, then at step S70 $n(D) \sim n(D_N)$ is displayed.

If in Equation (22) no solution is obtained because of a greater difference between the maximum value and the minimum value of the eigenvalues of $G(n_0)^* G(n)$, then use may be made of the constrained inversion method. This method is disclosed in detail in "The 1983 Dissertations Vol. 19, No. 10" of "Society of Instrument and Control Engineers" (Japan), the paper by K. Tatsuno Entitled "The Conversion of the Intensity Distribution of Scattering Light to the Droplet Size Distribution on a Droplet Size Measuring Apparatus using Laser Light". This paper discloses the solution of the least squares of Equation (19) which is found based on the first condition that the sum of the differences of third order for the droplet size distribution $n_1, n_2, \ldots, n_N$ is constant and on the second condition that $n_1, n_2, \ldots, n_N$ is constant and on the second condition that $n_1, n_2, \ldots, n_N$ are positive or zero.

That is, with the solution of the aforementioned first condition put as $$H = K^*K \tag{31}$$

and with $\gamma$ denoting an undetermined multiplier, the solution of Equation (19) is given by $$n = (G(n)^*G(n) + \gamma H)^{-1} G(n) I \tag{32}$$

through the Lagrange's method of undetermined multiplier. Here $$K = \begin{pmatrix} 0 & & & & & & \\ 0 & 0 & & & & & \\ 0 & 0 & 0 & & & \cdots & \\ 1 & -3 & 3 & -1 & 0 & & \\ 0 & 1 & -3 & 3 & -1 & 0 & \\ & & 0 & & & & \\ & & \vdots & & & & \\ & & \vdots & & & & \end{pmatrix} \tag{33}$$

With the geometric mean of the eigenvalues of $G(n)^*G(n)$ given as $\gamma$ of Equation (32), a proper constraint can be given.

It is necessary that, in order for n evaluated from Equation (32) to satisfy the second condition, n is meet the following condition.

<<Condition>>

$$y = G(n)^*(G(n) \times n - I) + \gamma \times H \times n$$

Thus $y_j \geq 0$ for j at $n_j = 0$ and $y_j = 0$ for j at $n_j > 0$

In this procedure the intensity distribution $I(\theta_f)$ of the scattered beams has to be found in terms of the light energy (absolute intensity distribution) as set forth below.

For the particles with the absolute droplet size distribution $n_p(D)$ as represented by their individual number, such as polystyrene particles and glass spheres, the absolute intensity distribution $I_p(\theta_f)$ of those scattering light, that is, the intensity distribution of the scattering light expressed in terms of the energy level of the light, can be calculated with the use of Equation (6). The intensity distribution of the scattering light on those particles is measured.

With the measured value as $I_{pm}(\theta_f)$, the conversion table $T(\theta_f)$ will be $$T(\theta_f) = \frac{I_p(\theta_f)}{I_{pm}(\theta_f)} \quad (\theta_f = \theta_1, \theta_2, \ldots, \theta_K) \tag{34}$$

If the measured value of the intensity distribution of the scattered light on the to-be-measured particles with their absolute droplet size distribution unknown is given by $I_m(\theta_f)$, then the absolute intensity distribution $I(\theta_f)$ of the scattered light can be found from Equation (34) as follows:

$$I(\theta_f) = T(\theta_f) \cdot I_m(\theta_f) \tag{35}$$

In this way, the absolute calibration is made for the system of measuring the intensity distribution of the scattered light and $I(\theta_f)$ can be found as the light energy level, thus obtaining the absolute particle size distribution as their individual number for n(D).

According to this invention, owing to the restricted scattering path length in the scattering zone, the scattered beams of the respective scattering angles are obtained as the integration values of the scattered beams for the respective scattering positions in the scattering zone, while considering the decrease of the scattered light beams in the scattering zone, so that it is possible to calculate an accurate scattering light intensity distribution and thus an accurate droplet size distribution by means of the apparatus of this invention.

What is claim is:

1. A droplet size measuring apparatus comprising:
   light source means for directing parallel light beams onto a group of particles to be measured in a predetermined scattering path length;
   measuring means, having photodetectors arranged for respective scattering angles, for measuring an intensity distribution of light beams scattered on the group of particles; and
   calculating means for calculating the droplet size distribution of the group of particles in accordance with the measured intensity distribution of the scattered light beams, an attentuation of a beam intensity of the parallel beams within a scattering zone, and scattering path length of the scattering zone.

2. The droplet size measuring apparatus according to claim 1, in which said calculating means calculates the droplet size distribution n(D) of said group of particles from the intensity distribution $I(\theta)$ of said measured scattered light beams on the basis of an expression $$I(\theta) = \int \{I_0 \exp(-l \int c(D) n(D) dD \cdot \int i(D, \theta + \theta_l) n(D) d(D)\} dl \tag{1}$$

where
$I_0$: an intensity of the parallel beams incident to the scattering zone;
l: a scattering position measured from the incident end of the scattering zone;
c(D): a scattering cross section of a particle with a diameter D;
$\theta$: a scattering angle measured at the center of the scattering zone;
$\theta + \theta_l$: the scattering angle measured at the scattering position l; and
$i(D, \theta + \theta_l)$: the intensity of the scattered beams on one particle.

3. The droplet size measuring apparatus according to claim 2, in which said calculating means calculates n(D) by assuming a distribution function for n(D) having unknown parameters, substituting the assumed distribution function into said Equation (1), and determining the unknown parameters with the use of the least squares method and Newton's method.

4. The droplet size measuring apparatus according to claim 2, in which said calculating means calculates n(D) by dividing an integration interval for the particle size D of Equation (1) into subintervals, regarding the Equation (1) as simultaneous equations on the assumption that n(D) within the subinterval is constant, and solving the simultaneous equations with the use of the least squares method and Newton's method.

* * * * *